United States Patent [19]
Williams et al.

[11] Patent Number: 4,862,735
[45] Date of Patent: Sep. 5, 1989

[54] MICROVISCOMETER

[75] Inventors: John G. Williams, Hatboro; Thomas M. Donnellan, Warminster; Ronald E. Trabocco, Blue Bell, all of Pa.

[73] Assignee: The United States of America as represented by the Secretary of the Navy, Washington, D.C.

[21] Appl. No.: 177,216

[22] Filed: Apr. 4, 1988

[51] Int. Cl.⁴ ............................................. G01N 11/10
[52] U.S. Cl. ............................................ 73/54; 73/59
[58] Field of Search ...................... 73/54, 59, 60, 32 A

[56] References Cited

U.S. PATENT DOCUMENTS

| 1,281,042 | 10/1918 | MacMichael | 73/59 |
| 2,340,507 | 2/1944 | Bjork | 73/59 |
| 2,484,761 | 10/1949 | Stock | 73/59 |
| 4,499,753 | 2/1985 | Carr | 73/59 |
| 4,535,621 | 8/1985 | Gervais et al. | 73/843 |
| 4,667,519 | 5/1987 | Burg et al. | 73/815 |
| 4,704,898 | 11/1987 | Thone | 73/54 |

FOREIGN PATENT DOCUMENTS

| 3306406 | 8/1984 | Fed. Rep. of Germany | 73/59 |
| 2257083 | 8/1975 | France | 73/54 |
| 0015838 | 1/1984 | Japan | 73/54 |

Primary Examiner—Stewart J. Levy
Assistant Examiner—Michele Simons
Attorney, Agent, or Firm—W. C. Townsend; John M. O'Meara; Susan E. Verona

[57] ABSTRACT

An apparatus is disclosed for determining the viscosity of fluids and for determining the point of gelation during the curing of a material. Attached to one end of an oscillating lever, a disposable probe is immersed in a small fluid specimen, while a strain gauge and a displacement transducer are attached to the lever for monitoring its movement. The viscosity of fluids is correlated with the strain measurement, while the gelation point of a material during its curing cycle is determined by monitoring the phase angle between the strain gauge output and the lever displacement transducer output.

6 Claims, 3 Drawing Sheets

MICROVISCOMETER

STATEMENT OF GOVERNMENT INTEREST

The invention described herein may be used by and for the Government of the United States of America for governmental purposes without the payment of any royalties thereon or therefor.

BACKGROUND OF THE INVENTION

This invention relates to an apparatus for measuring the viscosity of fluids and for determining the point of gelation during the curing of a material such as a resin. Viscometry is usually associated with measurement of flow rates of a fluid under constant pressure or with the direct measurement of shear stress and strain developed when the fluid is trapped between a moving plate or disc and a fixed plate or disc. Such techniques, however, have a limited viscosity range and are generally costly due to the requirement of precision machined parts. They also require a large fluid specimen, and viscometers for use in conjunction with resin curing process monitors must be operable with the small fluid samples used by the process monitors.

SUMMARY OF THE INVENTION

It is therefore an object of the invention to provide a viscometer with a broad viscosity range. Another object is to provide a viscometer for measuring the viscosity of small quantities of fluid. It is also an object to provide an apparatus for determining the point of gelation during the resin curing process. Other objects are to provide a less costly viscometer, and one with disposable probes.

Briefly, these and other objects of the invention are accomplished by a lever pivotally mounted near one end to a base. A disposable probe, consisting of a thin sheet of material attached to a wire support is connected to the one end of the lever. A constant speed motor oscillates the lever from side to side and sinusoidally with time about the pivot. The probe is aligned in the plane of oscillation of the lever and is immersed in the fluid specimen. Strain monitoring apparatus is arranged to measure strain along the longitudinal axis of the lever in a plane normal to its oscillation, while a transducer monitors the linear displacement of the probe, permitting viscosity to be measured. The point of gelation in a resin curing process may be measured by monitoring the phase angle between the strain monitoring apparatus output signal and the displacement transducer output signal.

BRIEF DESCRIPTION OF THE DRAWINGS

Other objects, advantages and novel features of the invention will become apparent from the following detailed description of the invention when considered in conjunction with the accompanying drawings wherein.

DESCRIPTION OF THE PREFERRED EMBODIMENT

Figure 1:
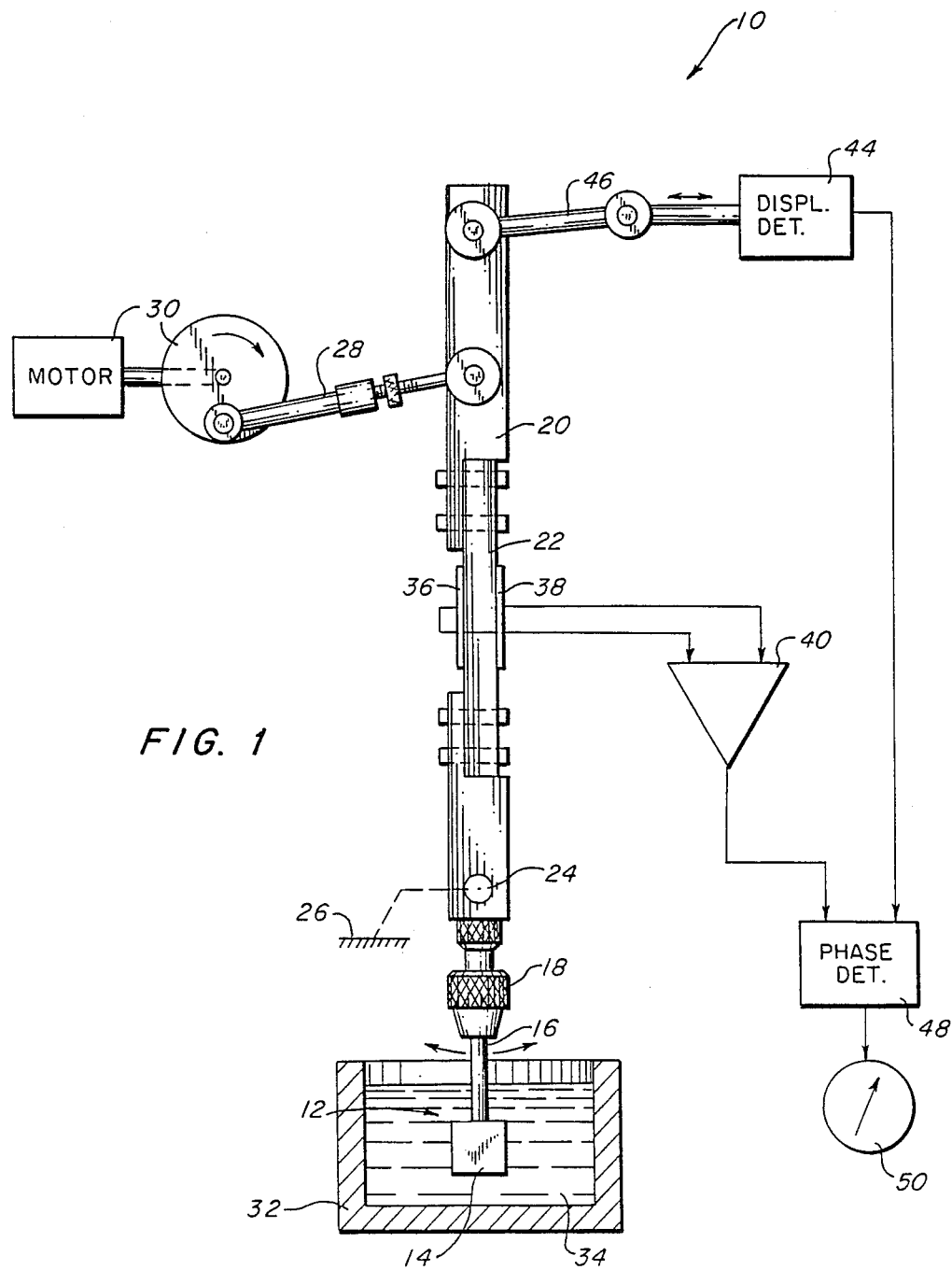
FIG. 1 illustrates a microviscometer in accordance with the present invention.

Various types of viscometers are well-known in the art, such as those which operate to measure the rate of flow of a fluid through an orifice or which measure the drag on a probe moving through the fluid. The present invention relates to the latter type of viscometer and incorporates means therein for monitoring strain developed in direct proportion to the drag on the probe. The preferred embodiment can best be understood by referring to the drawings wherein like characters designate like or corresponding parts throughout the views. A microviscometer, generally designated 10 is shown in FIG. 1, where a disposable probe 12, consisting of a thin sheet of material 14 rigidly attached to a wire 16, is detachably connected as by a chuck 18 to one end of a lever or member 20. Lever 20, or as shown a removable center portion 22 thereof, is made of a relatively flexible material such as polymethyl methacrylate, polycarbonate, or spring steel.

Lever 20 is pivotally mounted by a pin 24 near its probe end to a base 26, which is represented as a mechanical ground. A push rod 28 is connected at one end thereof to the end of lever 20 opposite probe 12. Constant speed motor 30 is eccentrically connected at the other end of push rod 28 in order to oscillate lever 20 from side to side to produce sinusoidal displacement thereof with time.

Probe 12 is aligned to have its predominant surfaces move in the plane of oscillatory of lever 20, and unit 10 is positioned so that probe 12 is immersed in a process monitor 32 containing a fluid specimen 34 throughout the full amplitude of each oscillation cycle. A strain measuring means is attached on center portion 22 and is arranged to measure tensile and compressive strain along the longitudinal axis of the lever 20 in a plane normal to its plane of oscillation. The strain measuring means may be two strain gauges 36 and 38, disposed on opposite sides of lever 20. A summing means 40, such as an operational amplifier, is connected to add the signals from strain gauges 36 and 38 in a conventional manner and outputs a signal indicative thereof. A transducer 44 monitors the displacement of lever 20 through an alignment compensating linkage 46 such as a pivot joint and may be a linear voltage differential transformer which provides an output voltage signal that varies with lever displacement. A phase angle detector 48 is connected to the output of displacement transducer 44 and the output of summing means 40 for the purpose of measuring the phase angle therebetween. A phase angle meter 50 is operatively connected to phase angle detector 48 for displaying a readout of the output therefrom.

Figure 2A:
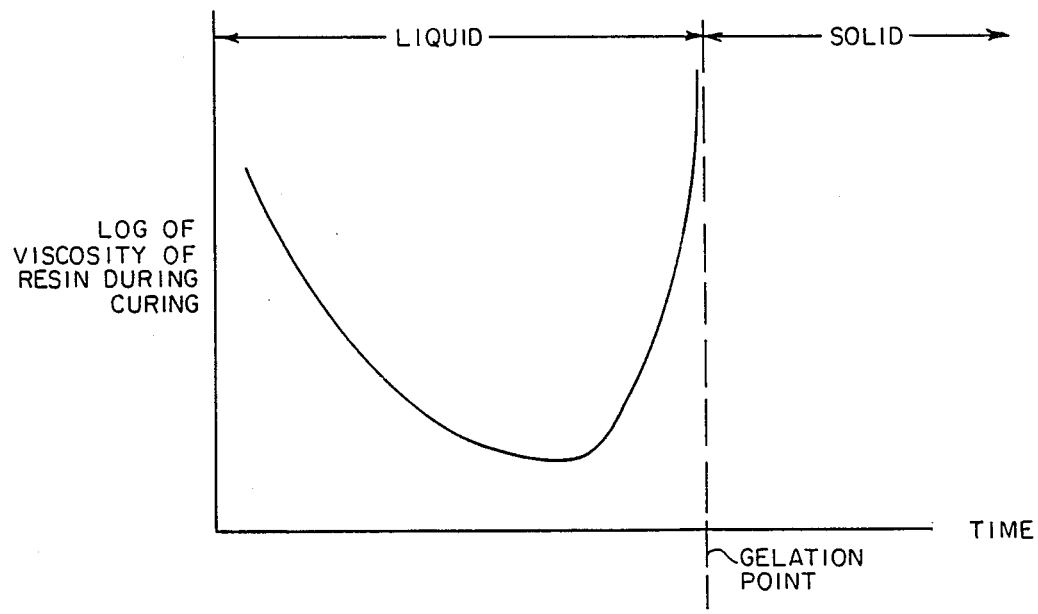
FIG. 2a is a plot of the log of the viscosity versus time for a typical resin curing process.
Figure 2B:
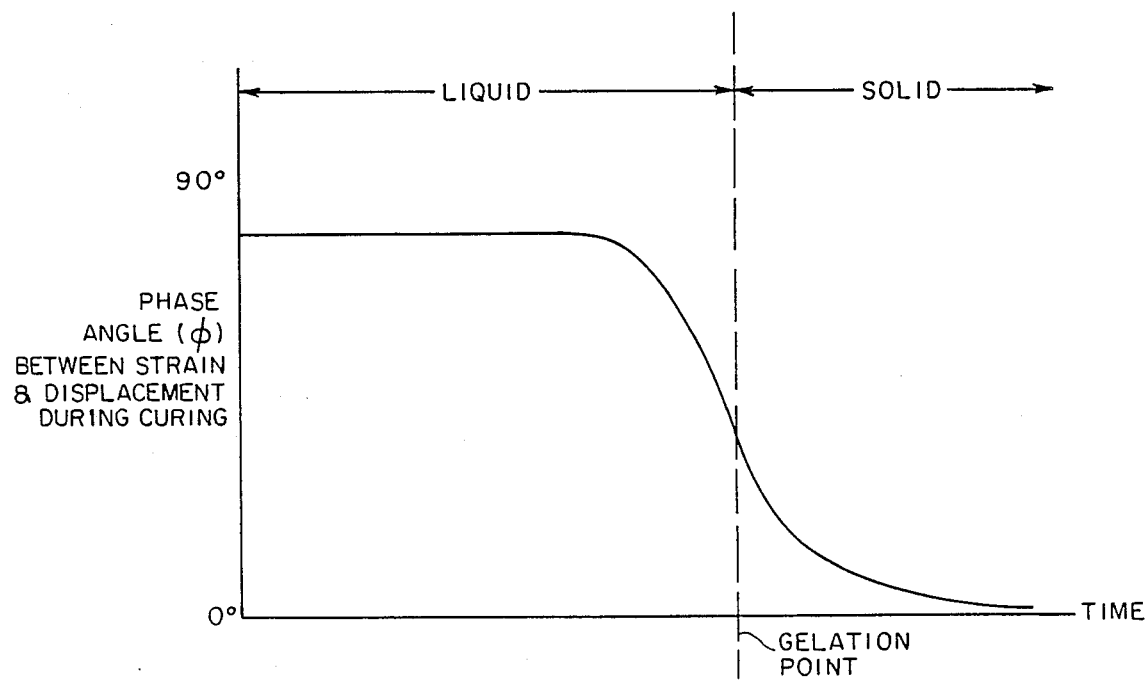
FIG. 2b is a plot of the phase angle change with time that occurs between strain and displacement for a typical resin curing process.
Figure 3A:
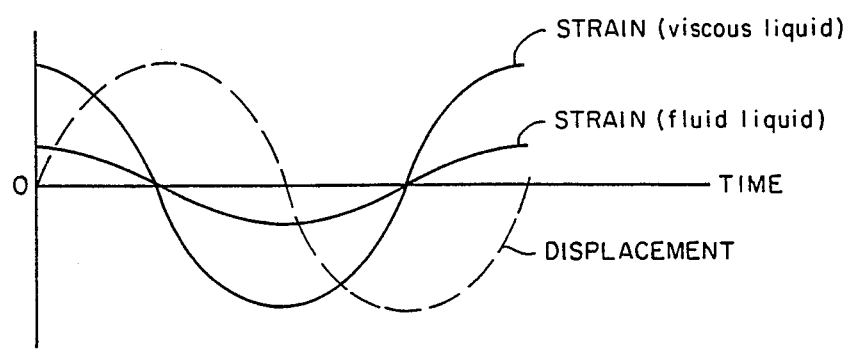
FIG. 3a is a plot of displacement superimposed on plots of strain for two different liquids as monitored with the microviscometer of FIG. 1.
Figure 3B:
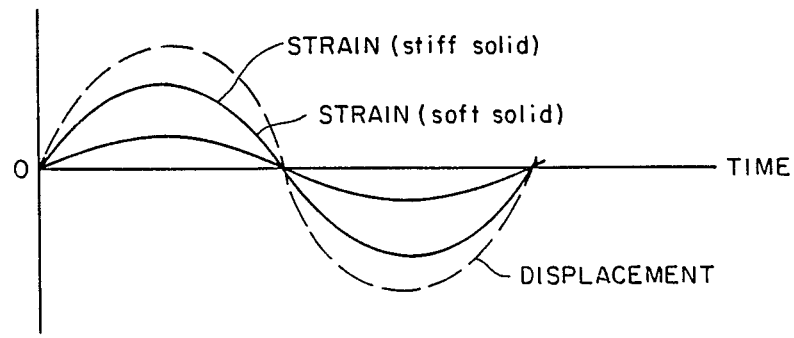
FIG. 3b is a plot of displacement superimposed on plots of strain for two different solids as monitored with the microviscometer of FIG. 1.

During operation of microviscometer 10, data on the viscosity of the fluid specimen 34 may be obtained by monitoring the magnitude of the output signals of strain gauge summing means 40 and displacement transducer 44. Microviscometer 10 may also be used to monitor the cure of a resin by monitoring the phase angle between the strain gauge summer output and the displacement transducer output. During the curing process the resin's viscosity decreases as it is heated to cure temperature and increases as the cure reaction proceeds, as shown in FIG. 2a. When the resin is liquid and the viscosity is low, as in the beginning of the process, the maximum strain gauge summer signal during oscillation will correlate closely with the midpoint of the displacement cycle, as shown in FIG. 3a, and the phase angle will then be large, as shown in FIG. 2b. After gelation, the gel will distort under the influence of the oscillation, the maximum signal from strain gauge summer 40 will more closely coincide with that of displacement, as shown in FIG. 3b, and the phase angle will be small, as shown in FIG. 2b. Therefore, by monitoring the phase angle during curing the point of gelation can be determined by observing when the phase angle changes from approximately 90° to approximately 0°, as shown in FIG. 2b. A comparison of FIGS. 3a and 3b also shows how the amplitude of the strain signal differs for liquids and solids, respectively, with different viscosity values.

Some of the many features and advantages of the invention should now be readily apparent. The microviscometer is not only capable of supplying data on the viscosity of a small fluid specimen, but can also indicate the point of cure or gelation for such materials as resins. Specifically, the probe can be used with cells of very small thickness, which is consistent with cells used to determine dielectric properties intended for use as process cure monitors. Used in conjunction with such a cure monitor, the microviscometer allows identification of dielectric parameters simultaneously with rheological data necessary for process control of curing resins. Furthermore, the microviscometer of the present invention does not require costly precision machined components upon which the accuracy of the instrument would depend, such as is the case with currently available equipment. Of course, when the chuck 18 is incorporated in the microviscometer 10 of this invention, the probe is disposable and need not be recovered from a cured specimen.

Having thus described the invention, it will be apparent to those skilled in the art that various modifications can be made within the spirit and scope of the present invention. Accordingly, it is intended to encompass all such modifications.

What is claimed is:

1. An instrument for detecting the gelation point of a material during the curing thereof, comprising:
   a base;
   a lever pivotally mounted to said base;
   means for oscillating said lever from side to side to produce a sinusoidal displacement rate about the pivot;
   a probe rigidly fixed to one end of said lever for immersion in the fluid sample, said probe being positioned in the oscillatory plane of said lever;
   means disposed on said lever for measuring and indicating strain along the longitudinal axis of said lever in a plane
   normal to the plane of oscillation; means for measuring and indicating the displacement of said lever during oscillaton; and
   means for monitoring the phase angle between the relative values of strain and displacement during oscillation of said lever to indicate the gelation point of the material as being when the phase angle changes from substantially 90° to substantially 0°.

2. An instrument according to claim 1, wherein said oscillating means comprises: a push rod pivotally connected at one end thereof to said lever; and
   a constant speed motor connected eccentrically to drive the other end of said push rod for translating angular to linear motion.

3. The instrument of claim 1 wherein the probe is configured of thin sheet-like material aligned in the plane of oscillation of said lever.

4. The instrument of claim 1 wherein the probe is detachably affixed to said lever.

5. An instrument for detecting the gelation point of a material during the curing thereof, comprising:
   a base;
   a lever pivotally mounted to said base;
   a constant speed motor operatively connected to said lever for producing side-to-side sinusoidal oscillation of said lever;
   a thin, sheetlike probe rigidly fixed to one end of said lever for immersion in the fluid sample, said probe being positioned in the plane of oscillation of said lever;
   a strain gauge disposed along the longitudinal axis of said lever to monitor strain in a plane normal to the oscillatory plane;
   a transducer connected to said lever for measuring and indicating the displacement of said lever during oscillation; and
   means for monitoring the plase angle between the relative values of strain and displacement during oscillation of said lever to indicate the gelation point of the material as being when the phase angle changes from substantially 90° to substantially 0°.

6. The instrument of claim 5 wherein the probe is detachably affixed to said lever.

* * * * *